United States Patent
Valous et al.

(10) Patent No.: US 11,501,444 B2
(45) Date of Patent: Nov. 15, 2022

(54) METHOD, SOFTWARE MODULE, AND INTEGRATED CIRCUIT FOR COLOR VISUALIZATION AND SEPARATION

(71) Applicant: UNIVERSITÄT HEIDELBERG, Heidelberg (DE)

(72) Inventors: Nektarios Valous, Heidelberg (DE); Niels Halama, Seeheim-Jugenheim (DE); Inka Zoernig, Frankfurt (DE); Dirk Jäger, Mainz-Kostheim (DE)

(73) Assignee: Universität Heidelberg, Heidelberg (DE)

( * ) Notice: Subject to any disclaimer, the term of this patent is extended or adjusted under 35 U.S.C. 154(b) by 34 days.

(21) Appl. No.: 17/045,723

(22) PCT Filed: Apr. 10, 2019

(86) PCT No.: PCT/EP2019/059095
§ 371 (c)(1),
(2) Date: Oct. 6, 2020

(87) PCT Pub. No.: WO2019/197472
PCT Pub. Date: Oct. 17, 2019

(65) Prior Publication Data
US 2021/0158529 A1    May 27, 2021

(30) Foreign Application Priority Data
Apr. 10, 2018   (EP) .................................... 18166482

(51) Int. Cl.
G09G 5/02      (2006.01)
G06T 7/11      (2017.01)
(Continued)

(52) U.S. Cl.
CPC .............. *G06T 7/11* (2017.01); *G06K 9/6256* (2013.01); *G06T 7/0012* (2013.01); *G06T 7/90* (2017.01);
(Continued)

(58) Field of Classification Search
CPC ... G06T 7/11; G06T 2207/10024; G06T 7/90; G06V 10/56; G06K 9/6256
See application file for complete search history.

(56) References Cited

U.S. PATENT DOCUMENTS
2014/0016853 A1   1/2014  Liu

OTHER PUBLICATIONS

The International Search Report (ISR) with Written Opinion for PCT/EP2019/059095 dated May 20, 2019, pp. 1-15.
(Continued)

*Primary Examiner* — Weiming He
(74) *Attorney, Agent, or Firm* — McDonnell Boehnen Hulbert & Berghoff LLP

(57) ABSTRACT

The present invention relates to a method for color visualization and separation of a natural and medical image comprising pixels defined by color pixel vector $a=[a_1 a_2, a_3]$ in a Cartesian color space (e.g. RGB), where the color pixel vector is represented by a pure quaternion $q=+a_1 i+a_2 j+a_3 k$ with i,j, k satisfying: $i^2=j^2=k^2=ijk=-1$, $ij=-ji=k, jk=-kj=i$, $ki=-ik=j$ and the image is decomposed into q+ and q using the orthogonal 2D planes split concept according to: (formula (I)) wherein/and g are pure unit quaternions or f and g describe interactively determined or computed colors ($s_1$, $s_2$). The method allows not only visualizing and separating certain colors in a digital image in a rapid fashion, but also permits a flexible definition pertinent to the kind of colors that can be visualized or separated by defining the corresponding decompositions by means of pure unit quaternions/and g. Colors $s_1$, $s_2$ can be defined manually or computed automatically from the image.

19 Claims, 6 Drawing Sheets

(51) Int. Cl.
*G06T 7/90* (2017.01)
*G16H 70/60* (2018.01)
*G16H 30/40* (2018.01)
*G06K 9/62* (2022.01)
*G06T 7/00* (2017.01)
*G06T 11/00* (2006.01)
*G06V 10/56* (2022.01)

(52) U.S. Cl.
CPC ............ *G06T 11/001* (2013.01); *G06V 10/56* (2022.01); *G16H 30/40* (2018.01); *G16H 70/60* (2018.01); *G06T 2207/30024* (2013.01); *G06T 2210/41* (2013.01); *G06V 2201/03* (2022.01)

(56) References Cited

OTHER PUBLICATIONS

Sangwine, Stephen J. et al. "Linear Colour-Dependent Image Filtering based on Vector Decomposition" European Signal Processing Conference, (2002), pp. 1-4.

Lan, Rushi et al. "Quaternion Decomposition Based Discriminant Analysis for Color Face Recognition" IEEE International Conference on Systems (2016) pp. 001833-001837.

Hitzer, Eckhard et al. "General two-sided quaternion Fourier transform, convolution and Mustard convolution" Advances in Applied Clifford Algebras 27 (2016), pp. 381-395.

Macenko, Marc et al. "A Method for Normalizing Histology Slides for Quantitative Analysis" BioMedical Imaging: from Nano to Macro (2009), pp. 1107-1110.

$f$ or $g = \mu_1 = i$, $|\mu_1| = 1$
$\mu_1: \rightarrow$ $f$ or $g = \mu_2 = j$, $|\mu_2| = 1$
$\mu_2: \rightarrow$ $f$ or $g = \mu_3 = k$, $|\mu_3| = 1$
$\mu_3: \rightarrow$ $f$ or $g = \mu_4 = \dfrac{i+j}{\sqrt{2}}$, $|\mu_4| = 1$
$i: \rightarrow, j: \rightarrow, k: \rightarrow, \mu_4: \dashrightarrow$ $f$ or $g = \mu_5 = \dfrac{i+k}{\sqrt{2}}$, $|\mu_5| = 1$
$i: \rightarrow, j: \rightarrow, k: \rightarrow, \mu_5: \dashrightarrow$ $f$ or $g = \mu_6 = \dfrac{j+k}{\sqrt{2}}$, $|\mu_6| = 1$
$i: \rightarrow, j: \rightarrow, k: \rightarrow, \mu_6: \dashrightarrow$ $f$ or $g = \mu_7 = \dfrac{i+j+k}{\sqrt{3}}$, $|\mu_7| = 1$
$i: \rightarrow, j: \rightarrow, k: \rightarrow, \mu_7: \dashrightarrow$ $f$ or $g = \mu_8 = \dfrac{-i+j}{\sqrt{2}}$, $|\mu_8| = 1$
$i: \rightarrow, j: \rightarrow, k: \rightarrow, \mu_8: \dashrightarrow$ $f$ or $g = \mu_9 = \dfrac{-i+k}{\sqrt{2}}$, $|\mu_9| = 1$
$i: \rightarrow, j: \rightarrow, k: \rightarrow, \mu_9: \dashrightarrow$ $f$ or $g = \mu_{10} = \dfrac{-j+k}{\sqrt{2}}$, $|\mu_{10}| = 1$
$i: \rightarrow, j: \rightarrow, k: \rightarrow, \mu_{10}: \dashrightarrow$ $f$ or $g = \mu_{11} = \dfrac{-i+j+k}{\sqrt{3}}$, $|\mu_{11}| = 1$
$i: \rightarrow, j: \rightarrow, k: \rightarrow, \mu_{11}: \dashrightarrow$ $f$ or $g = \mu_{12} = \dfrac{i-j+k}{\sqrt{3}}$, $|\mu_{12}| = 1$
$i: \rightarrow, j: \rightarrow, k: \rightarrow, \mu_{12}: \dashrightarrow$ $f$ or $g = \mu_{13} = \dfrac{i+j-k}{\sqrt{3}}$, $|\mu_{13}| = 1$
$i: \rightarrow, j: \rightarrow, k: \rightarrow, \mu_{13}: \dashrightarrow$

Fig. 3

METHOD, SOFTWARE MODULE, AND INTEGRATED CIRCUIT FOR COLOR VISUALIZATION AND SEPARATION

CROSS REFERENCE TO RELATED APPLICATION

This application is a U.S. National Phase of International Application No. PCT/EP2019/059095, filed Apr. 10, 2019, which claims priority to European Patent Application No. 18166482.2, filed Apr. 10, 2018, both of which are incorporated by reference herein in their entirety.

The present invention relates to a method, a software module, and an integrated circuit for color visualization and separation. The present invention relates particularly to a method, software module, and an integrated circuit for medical image analysis.

BACKGROUND OF THE INVENTION

Color separation and visualization is resource and time consuming, therefore there is a need for rapid (real-time or near real-time) and efficient solution of these issues.

The automatic analysis of images is important in many fields like medicine, scientific research, social media, multimedia and graphics, aeronautics, deep sea and space exploration, computational photography, etc.

In medical diagnostics and in particular in pathomics, specifically marked antibodies are used to stain proteins in situ. Analyzing the intensity and distribution of stained tissue at specific locations of interest can provide clinically important information regarding disease (e.g. cancer) diagnosis or prognosis. The common practice in the clinic is the visual scoring of stains using a light microscope with medium-power magnification. However, visual scoring is time consuming and may be subjective.

Computer-assisted analysis of stained tissue shortens processing time and lessens inter-observer variation. Image analysis of stains is generally performed by differentiating staining components, e.g. the immunoreaction product (brown; diaminobenzidine) and hematoxylin as the counterstain (blue). Visualizing and separating stains is an important process in the field of pathomics, e.g. qualitative and quantitative analysis of stained tissue.

Digital images in medical diagnostics can be used to make primary diagnoses, for repeated assessments, telepathology, quality assurance, archiving and sharing, education and conferencing, image analysis, research and publications, marketing and business purposes, as well as tracking. The digital imaging process includes four key steps: image acquisition, storage and management, manipulation and annotation, and viewing or transmission of images.

Pathology typically involves clinicians examining images, extracting relevant information, and rendering diagnostic decisions. Besides morphology, color represents the major guiding parameter for the evaluating physician (or algorithm). The processing of images for the identification of specific colors is, for example, performed using color deconvolution algorithms; these require plenty of resources and can have relatively long computation times. The identification of specific colors in color images represents a bottleneck that slows down the evaluation phase significantly. The larger the image, typically the more computing resources and time is required for identifying specific colors.

The pixels of an image can be represented by quaternions. Quaternions are hypercomplex numbers with one real and three imaginary parts. Color can be perceived as three coordinates relative to an origin that is often chosen to match black. Therefore, a color can be defined by a vector from black with orientation and magnitude to reach any point in a coding space. As an example, color can be represented by vectors constructed by a linear combination of three primaries; in a Cartesian color space, e.g. RGB the basic element i is chosen to describe red, j green, and k blue. As any color is encoded by a linear combination of the primaries, color pixels can be encoded by a linear combination of the three basis vectors in a hypercomplex algebra framework, i.e. quaternions. This provides the opportunity to process color images in a geometric way, and hence the quaternionic representation of color allows image processing and analysis to be performed in a more coherent manner.

Sangwine et al. ("Linear colour-dependent image filtering based on vector decomposition"; $11^{th}$ European Signal Processing Conference; Sep. 3-6, 2002, Toulouse, France) pertains to quaternion mathematics and presents an application pertinent to filtering.

Lan and Zhou ("Quaternion Decomposition Based Discriminant Analysis for Color Face Recognition"; IEEE International Conference on Systems, Man, and Cybernetics SMC 2016; Oct. 9-12, 2016, Budapest, Hungary) also pertains to quaternion mathematics but defines the components as parallel and vertical for their subsequent use in face recognition.

Hitzer ("General two-sided quaternion Fourier transform, convolution and Mustard convolution"; Adv. Appl. Clifford Algebras 27; May 12, 2016, p. 381-395) reports improved two-sided quaternionic Fourier transformation.

The prior art identified above does not identify color visualization and separation in images as a potential application and fails to describe unsupervised or supervised color visualization (re-colorization and decolorization) or color separation in natural and medical images.

The present invention offers a simple, rapid, and flexible method of digitally visualizing and separating staining information in the framework of hypercomplex (quaternion) algebras. Essentially, the objective of the present invention is to provide a fast and efficient solution for visualizing and identifying certain colors in an image. The objective is fulfilled by the subject matter according to the independent claims. Preferable implementations are provided in the corresponding sub-claims.

SUMMARY OF THE INVENTION

The invention provides a method for color visualization and separation of an image comprising pixels defined by color pixel vector $a=[a_1, a_2, a_3]$ in a Cartesian color space (e.g. RGB), where the color pixel vector is represented by a pure quaternion $q=a_1 i + a_2 j + a_3 k$ with i, j, k satisfying:

$$i^2 = j^2 = k^2 = ijk = -1, ij = -ji = k, jk = -kj = i, ki = -ik = j$$

and the image is decomposed into $q_+$ and $q_-$ using the orthogonal 2D planes split concept according to:

$$q_+ = \tfrac{1}{2}(q + fqg), q_- = \tfrac{1}{2}(q - fqg)$$

where f and g are pure unit quaternions.

Quaternion algebra provides the framework for decomposing a color image using the orthogonal 2D planes split concept. This is particularly useful for color visualization and separation of digital images where the pixels are represented by vectors. These vectors can be decomposed and thus it is possible to extract color information from an image.

The method not only allows visualizing and separating certain colors in a digital image in a rapid fashion, but also permits a flexible definition pertinent to the kind of colors that can be visualized or separated by defining the corresponding decompositions by means of pure unit quaternions f and g. Preferably, f and g are pure unit quaternions, or f and g describe interactively determined or computed colors $s_1$, $s_2$. Colors $s_1$, $s_2$ can be defined manually or computed automatically from the image.

The pixels in $q_+$ and $q_-$ can be converted into a triplet (three real numbers) where each triplet forms the color channels R (red), G (green), and B (blue). The values of each triplet can be arranged in matrices forming an n×m×3 array where (n, m) are the coordinates of the corresponding pixel in the image.

The real numbers of the matrix or the entire array can be normalized to a predefined range and in particular to the range of 0 to 1. In addition, the real numbers of the matrix can be truncated to zero if they are less than 0 and to one if they are larger than 1; such step is carried out for the separation of the colors.

After processing, the three matrices can be concatenated to a color image or each color channel can be analyzed independently.

A pre-processing step can be carried out before the image is decomposed which includes:
- The operation [ln(q) exp (q)] for each pure quaternion q.
- Converting the quaternions to triplets where each triplet defines the three-color channels R, G, and B, and normalizing the values of the resulting matrices to a predefined range: 0 to 1.

One or more of the aforementioned methods are sequentially carried out, where in a first run no color separation is carried out, and in a second or further run a color separation step is carried out. In such a sequence, the same method can be repeated, or different methods can be sequentially carried out. All methods comprise the step of decomposing the image using the orthogonal 2D planes split concept. Methods may differ in that different pure unit quaternions f and g are used for the decomposition, or methods comprise additional steps such as the steps described above.

Thus, by conveniently rewriting the quaternionic representation of images considering geometric considerations with simple algebraic operations, it is feasible to mathematically decompose a stained tissue image into different spectral representations that can visualize and separate the chromogen information encoded in the stains. This pixel-based approach is computationally efficient, taking advantage of parallel architectures in modern computing systems (e.g. processors and graphics cards). The benefits can be translated in two components: i) as a means for better manual assessment (e.g. easier identification of hotspots and weak staining, etc.) of the stained tissue by clinicians (visualization), and ii) as a key step of digitally separating stained areas for further quantification (separation).

Essentially, the contribution of the present invention—in the visualization phase—is to provide e.g. clinicians or scientists (in real-time or near real-time) robust and case-invariant alternative visual representations of images of stained tissue. The contribution of the present invention—in the separation phase—is to provide e.g. clinicians or scientists or algorithms simple and rapid separation of specific colors in stained tissue images. By this, it can positively influence expert interpretation (or algorithmic implementation) thus providing consistent, accurate, and efficient diagnostic performance, which in turn can reduce the needs for extensive dedicated training and increase the visual expertise of the clinicians or efficiency of automated algorithmic workflows.

According to a first aspect, the present invention provides a method for color visualization and separation of a natural and medical image comprising pixels defined by color pixel vector a=[$a_1$, $a_2$, $a_3$] in a Cartesian color space. The color pixel vector is represented by a pure quaternion q=$a_1$i+$a_2$j+$a_3$k with i, j, k satisfying:

$$i^2=j^2=k^2=ijk=-1, ij=-ji=k, jk=-kj=i, ki=-ik=j$$

and the image is decomposed into $q_+$ and $q_-$ using the orthogonal 2D planes split concept according to:

$$q_+=\tfrac{1}{2}(q+fqg), q_-=\tfrac{1}{2}(q-fqg)$$

Thereby, f and g can be pure unit quaternions, or f and g describe interactively determined or computed colors ($s_1$, $s_2$).

According to one embodiment, the determined or computed colors can be contained in the image.

According to one embodiment, f=g or f≠g.

According to one embodiment, f and g can correspond to one or more of the following pure unit quaternions:

$$\mu_1 = i, \mu_2 = j, \mu_3 = k, \mu_4 = \frac{i+j}{\sqrt{2}}, \mu_5 = \frac{i+k}{\sqrt{2}}, \mu_6 = \frac{j+k}{\sqrt{2}},$$

$$\mu_7 = \frac{i+j+k}{\sqrt{3}}, \mu_8 = \frac{-i+j}{\sqrt{2}}, \mu_9 = \frac{-i+k}{\sqrt{2}}, \mu_{10} = \frac{-j+k}{\sqrt{2}},$$

$$\mu_{11} = \frac{-i+j+k}{\sqrt{3}}, \mu_{12} = \frac{i-j+k}{\sqrt{3}}, \mu_{13} = \frac{i+j-k}{\sqrt{3}}$$

Preferably, f and g each independently corresponds to one of the above pure unit quaternions.

Preferably, f and g are pure unit quaternions $\mu_a$ or $\mu_a\mu_b$ or $\mu_a\mu_b\mu_c$ where a, b, and c are integers from 1 to 13.

According to one embodiment, the color space can Cartesian and is preferably RGB.

According to one embodiment, $q_+$ and $q_-$ can be converted into sets of real numbers where each form one of three color channels R (red), G (green), and B (blue). Preferably, the real numbers are either normalized to a predefined range or truncated to zero if they are less than 0 and are truncated to one if they are larger than 1.

According to one embodiment, multiple color visualization and separation steps are iteratively carried out for complex color separation workflows.

According to one embodiment, color visualization results in performance enhancements (classification) for supervised machine learning workflows.

According to one embodiment, color visualization and separation is carried out in the fields of medical image analysis, scientific research, social media, multimedia and graphics, aeronautics, deep sea and space exploration, computational photography.

According to one embodiment, implementation provides additional scientific/technological insights, creates a product with new functionality or enhances a product with additional functionality, and augments tissue and cell diagnostic workflows and pipelines.

According to a second aspect, the present invention provides a software module, wherein the software module is implemented to carry out the method according to the present invention.

According to a third aspect, the present invention provides an integrated circuit, wherein the integrated circuit is implemented to carry out the method according to the present invention.

According to a fourth aspect, the present invention provides a device for image analysis, comprising: a camera, a computational unit, a display unit and an input unit, wherein the computational unit comprises the software module and/or the integrated circuit according to the present invention.

However, the use of the present invention is not limited to clinical or medical use. Rather, the present invention can be used in any kind of process, where certain colors or color combinations can be visualized and separated from a color image, e.g. in scientific research, social media, multimedia and graphics, etc.

BRIEF DESCRIPTION OF THE FIGURES

Examples of the present invention are described below in more detail by means of accompanying figures:

FIG. 3: Pure unit quaternions with the corresponding graphs which can be used for color visualization and separation according to a method of the present invention.

DETAILED DESCRIPTION OF EMBODIMENTS

Figure 1:
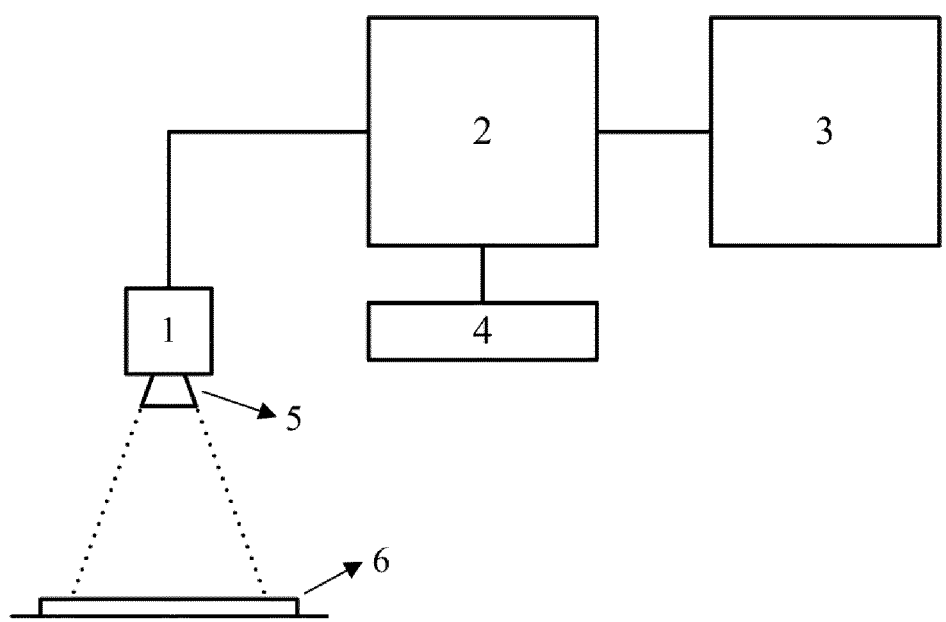
FIG. 1: Schematic of a device for color visualization and separation.

A device for carrying out the method according to the present invention is schematically shown in FIG. 1 and comprises a camera 1, a computational unit 2, a display unit 3 and an input unit 4. The computational unit 2 is usually implemented as a standalone computing device and the input unit 4 as a keyboard or other input device. However, it is also possible that the computational unit 2 is integrated into the camera 1. In such implementation, the computational unit preferably comprises an embedded computing system.

Camera 1 comprises a lens system 5 which is directed to a probe 6 for scanning the probe 6. In the present implementation as shown in FIG. 1, the probe 6 is a planar item. Camera 1 can be incorporated in any kind of microscope. Camera 1 can also be incorporated in a medical catheter for scanning vessels of a human or animal body. In such a case a light source is provided for illuminating probe 6. In the computational unit 2, a software module for carrying out a method for color visualization and separation of an image is stored and executed.

The method according to the present invention is based on quaternion algebra. The basic algebra of quaternions is described in J. P. Morais et al., *Real Quaternionic Calculus Handbook*, Springer, Basel, 2014, Chapter 1. The algebra $\mathbb{H}$ of real quaternions is a four-dimensional (4D) non-commutative algebra over the real number field $\mathbb{R}$ with canonical basis 1, i, j, k satisfying:

$$i^2=j^2=k^2=ijk=-1, ij=-ji=k, jk=-kj=i, ki=-ik=j \qquad (1)$$

The quaternion can be viewed as a 4D vector space defined over the real numbers. The quaternion is also the generalization of the conventional complex number and consists of four components: one real and three imaginary parts. A quaternion is often represented in the following form:

$$q=q_r+q_i i+q_j j+q_k k \qquad (2)$$

where $q_r, q_i, q_j,$ and $q_k \in \mathbb{R}$. From Eq. 2, $q_r$ is called the real (scalar) part and $q_i i + q_j j + q_k k$ is called the vector part. The conjugate of a quaternion leaves the scalar part unchanged and is defined as:

$$\tilde{q}=q_r-(q_i i+q_j j+q_k k) \qquad (3)$$

The norm of a quaternion is given by:

$$|q|=\sqrt{q_r^2+q_i^2+q_j^2+q_k^2} \qquad (4)$$

Essentially, when $q_r=0$ then q is a pure quaternion. When $|q|=1$ and $q_r=0$ then q is a pure unit quaternion. Arithmetic and algebraic operations with quaternions are described in the *Real Quaternionic Calculus Handbook*. A split of quaternions is motivated by the consistent appearance of two terms in the quaternion Fourier transform:

$$F\{f\}(u,v)=\int_{\mathbb{R}^2} e^{-i\mu x}f(x,y)e^{-j v y} dx dy \qquad (5)$$

This observation (i is on the left and j is on the right) and that every quaternion can be rewritten as:

$$q=q_r+q_i i+q_j j+q_k k=q_r+q_i i++q_k ij \qquad (6)$$

motivated the quaternion split with respect to the pair of orthonormal pure unit quaternions i, j:

$$q=q_++q_-, q_\pm=\tfrac{1}{2}(q \pm iqj) \qquad (7)$$

Figure 2:
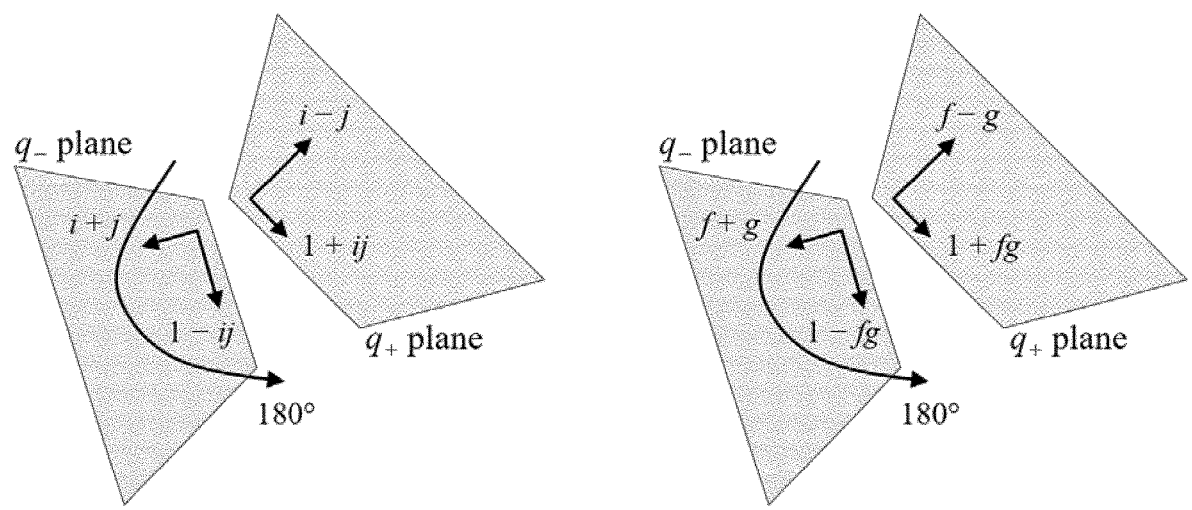
FIG. 2: Geometric illustration of the involutions $i \cdot (\ ) \cdot j$ and $f \cdot (\ ) \cdot g$ where the map $i \cdot (\ ) \cdot j$ rotates the $q_-$ plane by 180° around the 2D $q_+$ axis plane (left), and similarly for $f \cdot (\ ) \cdot g$ (right).

Basically, replacing e.g. i with j, and j with k throughout would merely change the notation but not the fundamental observation. This quaternion split is called the orthogonal 2D planes split (FIG. 2). Detailed information regarding the orthogonal 2D planes split of quaternions can be found in E. Hitzer et al., *Quaternion and Clifford Fourier Transforms and Wavelets*, Springer, Heidelberg, 2013, Chapter 2.

Given any two quaternions p, q and applying the orthogonal 2D planes split, the resulting two parts are orthogonal. The map $i \cdot (\ ) \cdot j$ leads to an adapted orthogonal basis of $\mathbb{H}$:

$$iqj=q_+-q_- \qquad (8)$$

Under the map $i \cdot (\ ) \cdot j$, the $q_+$ part is invariant but the $q_-$ part changes sign. Both parts are 2D and span two orthogonal planes, hence the name orthogonal planes split. The $q_+$ and $q_-$ plane have the orthogonal quaternion basis:

$$q_+: \{i-j=i(1+ij), 1+ij=1+k\}, q_-: \{1+j=i(1-ij), 1-ij=1-k\} \qquad (9)$$

All four basis quaternions $\{1-j, 1+ij, 1+j, 1-ij\}$ form an orthogonal basis of $\mathbb{H}$ interpreted as $\mathbb{R}^4$. A geometric picture is obtained on the left side of FIG. 2. The map $i \cdot (\ ) \cdot j$ rotates the $q_-$ plane by 180° around the 2D $q_+$ axis plane. In agreement with the geometric interpretation, the map $i \cdot (\ ) \cdot j$ is an involution because applying it twice leads to identity:

$$i(iqj)j=i^2qj^2=(-1)^2q=q \qquad (10)$$

Assuming an arbitrary pair of pure unit quaternions f and g, then the orthogonal 2D planes split is defined with respect to any pure unit quaternion f and g as:

$$q_\pm = \tfrac{1}{2}(q \pm fqg), fqg = q_+ - q_- \quad (11)$$

Under $f \cdot (\ ) \cdot g$ the $q_+$ part is invariant but the $q_-$ part changes sign. Both parts are 2D and span two orthogonal planes. For $f \pm g$, the $q_+$ and $q_-$ plane is spanned by two orthogonal quaternions, respectively:

$$q_+ : \{f-g, 1+fg=-f(f-g)\}, q_- : \{f+g, 1-fg=-f(f+g)\} \quad (12)$$

For $f=g$, a fully orthonormal 4D basis of $\mathbb{H}$ is the following:

$$\{1, f, j', k'\} = [i(i+f)]^{-1}(1, i, j, k)[i(i+f)], q_+ : \{j', k'\}, q_- : \{1, f\} \quad (13)$$

Given any two quaternions p and q and applying the orthogonal 2D planes split with respect to any two pure unit quaternions f and g we get zero for the scalar part of the mixed products. Any 2D plane in $\mathbb{R}^4$ determines the orthogonal planes split and vice versa. For the geometric interpretation of the map $f \cdot (\ ) \cdot g$, see the right side of FIG. 2; it rotates the $q_-$ plane by 180° around the $q_+$ axis plane.

Image pixels in a Cartesian color space (e.g. RGB) have three components and they can be represented in quaternion form using pure quaternions. For example, a pixel at coordinates (n, m) in a color image q can be represented as:

$$q(n, m) = r(n, m)i + g(n, m)j + b(n, m)k \quad (14)$$

where r(n, m), g(n, m), and b(n, m) are the red, green, and blue components of the pixel, respectively.

The choice of the imaginary part of the quaternion to represent pixel values is determined by interpreting color pixels as vectors. The imaginary part of a quaternion has three components and can also be associated with a 3-space vector. In this way, the color image is represented as a matrix of size n×m whose elements are pure quaternions. Although real and complex number systems are used to provide arithmetic operations of 1D and 2D data, quaternions can handle algebraic operations of ternary numbers, ergo expressing color data directly.

As stated above, quaternions can be conveniently decomposed through the orthogonal 2D planes split with respect to any pure unit quaternions f and g. The $q_+$ and $q_-$ plane decompositions are defined as:

$$q_+ = \tfrac{1}{2}(q+fqg), q_- = \tfrac{1}{2}(q-fqg) \quad (15)$$

In these decompositions, the inventors define the map $f \cdot (\ ) \cdot g$ to be a combination of pure unit quaternions $\mu_1$ to $\mu_{13}$ that derive from the pure quaternions: i, j, k, i+j, i+k, j+k, and i+j+k, respectively. For example, $\mu_7$ in the RGB color space is the direction corresponding to the luminance axis. The symbol ( ) refers to a color pixel in pure quaternion form. The equations are shown in FIG. 3 with the corresponding graphs.

The initial choice of the pure unit quaternions f and g is based on the notion that f=g, namely:

$\mu_1 \cdot (\ ) \cdot \mu_1, \mu_2 \cdot (\ ) \cdot \mu_2, \mu_3 \cdot (\ ) \cdot \mu_3, \mu_4 \cdot (\ ) \cdot \mu_4, \mu_5 \cdot (\ ) \cdot \mu_5, \mu_6 \cdot (\ ) \cdot \mu_6$, and $\mu_7 \cdot (\ ) \cdot \mu_7$.

The final choice of f and g is based on the notion that f≠g. In these decompositions, $f \cdot (\ ) \cdot g$ is generalized to be combinations of the pure unit quaternions $\mu_1$ to $\mu_{13}$. In the first instance, f and g each are equal to single pure unit quaternions (e.g. $f=\mu_1$ and $g=\mu_2$), namely (f<g for avoiding duplicates):

$\mu_1 \cdot (\ ) \cdot \mu_2, \mu_1 \cdot (\ ) \cdot_3, \mu_1 \cdot (\ ) \cdot \mu_4, \mu_1 \cdot (\ ) \cdot \mu_5, \mu_1 \cdot (\ ) \cdot \mu_6, \mu_1 \cdot (\ ) \cdot \mu_7,$
$\mu_2 \cdot (\ ) \cdot \mu_3, \mu_2 \cdot (\ ) \cdot \mu_5, \mu_2 \cdot (\ ) \cdot \mu_5, \mu_2 \cdot (\ ) \cdot \mu_7, \mu_3 \cdot (\ ) \cdot \mu_4, \mu_3 \cdot (\ ) \cdot \mu_5,$
$\mu_3 \cdot (\ ) \cdot \mu_6, \mu_3 \cdot (\ ) \cdot \mu_7, \mu_4 \cdot (\ ) \cdot \mu_5, \mu_4 \cdot (\ ) \cdot \mu_6, \mu_4 \cdot (\ ) \cdot \mu_7, \mu_5 \cdot (\ ) \cdot \mu_6,$
$\mu_5 \cdot (\ ) \cdot \mu_7$, and $\mu_6 \cdot (\ ) \cdot \mu_7$.

In the final instance, f and g each are equal to a single or the product of two or three pure unit quaternions, e.g. $f = f_A f_B = \mu_1 \mu_2$ and $g = g_A g_B = \mu_4 \mu_6$ ($f_A < f_B \leq g_A < g_B$ plus the properties of quaternion multiplication for avoiding duplicates). Combinations are numerous and not shown due to space considerations.

The algebra of quaternions is applied by the method according to the present invention for color visualization and separation of an image comprising pixels defined by color pixel vector $a=[a_2, a_3]$ in a Cartesian color space (e.g. RGB). The color pixel vector is represented by the pure quaternion $q = a_1 i + a_2 j + a_3 k$ and the image is visualized and separated using the orthogonal 2D planes split concept to $q_+$ and $q_-$. This allows the decomposition of an image into $q_+$ and $q_-$ by selecting appropriate pure unit quaternions. This computation can be carried out in few steps and thus quickly with a computing device. This is a pixel-based approach, hence can be parallelized and executed rapidly by modern processors and graphic cards.

EXAMPLES

Examples are provided in FIGS. 4 to 6 by applying a method according to the present invention for color visualization and separation of an image.

The first example A1 is a method for the visualization of certain colors in an image. This example comprises the following steps:

Input a color image (elements $\in \mathbb{R}$) and convert to a quaternion matrix (elements $\in \mathbb{H}$).

Perform the orthogonal 2D planes split using any pure unit quaternion combination of interest from $\mu_1$ to $\mu_{13}$ (elements $\in \mathbb{H}$).

Convert quaternion matrix to three real matrices corresponding to the three-color channels R, G, and B (elements $\in \mathbb{R}$).

Normalize the values of each matrix or entire array to the range 0 to 1 using corresponding minimum and maximum values (elements $\in \mathbb{R}$).

Concatenate the three matrices into one and output a color image (elements $\in \mathbb{R}$).

A color image (e.g. RGB) comprises pixels each having three components which represent values for the colors red, green and blue. The pixels form an array and pixel coordinates (n, m) are assigned. According to Eq. 14 each pixel can be represented by a quaternion q(n, m).

In the first step of this example a color image is the input. In the second step, the pixels are converted into quaternions q(n, m) and arranged in a matrix of size n×m whose elements are pure quaternions. Then the orthogonal 2D planes split is carried out using a combination of pure unit quaternions ($\mu_1$ to $\mu_{13}$). In physical terms, this corresponds to the decomposition of an image into two images ($q_+$, $q_-$) with different colors with respect to the original image. By suitable selection of f and g different spectral representations of the original image can be generated.

Then the images ($q_+$, $q_-$) are converted each to three matrices corresponding to the three-color channels R, G and B. The three components of the pure quaternion describing the pixels are extracted according to Eq. 14, so the factor r is the intensity of red, the factor g is the intensity of green, and the factor b is the intensity of blue. The matrix of color channel R with coordinates (n, m) comprises all factors r. Corresponding matrices are generated for G and B.

The values of each matrix or entire array are normalized to the range 0 to 1 using the corresponding minimum and maximum values. In the normalization step the intensity of the three colors is changed. The three matrices are then merged to a color image for each ($q_+$, $q_-$), thus consisting of the output.

With this method the original image can be decomposed quickly by defining f and g so that certain colors are emphasized. This is particularly advantageous for analyzing images of probes which have one or more colors. The vectors f and g are selected in such a way so that the colors of interest are readily emphasized.

A second example B1a is a method for separating certain colors in an image:

Input a color image (elements $\in \mathbb{R}$) and convert to a quaternion matrix (elements $\in \mathbb{H}$).

Perform the orthogonal 2D planes split using any pure unit quaternion combination of interest from $\mu_1$ to $\mu_{13}$ (elements $\in \mathbb{H}$).

Convert quaternion matrix to three real matrices corresponding to the three-color channels R, G, and B (elements $\in \mathbb{R}$).

Truncate the values of each matrix that are less than 0 to zero and those larger than 1 to one (elements $\in \mathbb{R}$).

Concatenate the three matrices into one and output a color image (elements $\in \mathbb{R}$).

The second example B1a corresponds substantially to first example A1 but differs only in the step of normalizing the values which is replaced by the step of truncating the values of each matrix. The values that are less than zero are truncated to zero, and those that are larger than one, are truncated to one. By this method the background is homogenized so that the colors are easier to separate.

Furthermore, instead of concatenating the three matrices into a color image, the three-color channels can be viewed separately as well. This applies for all other implementations described herein.

Figure 4A:
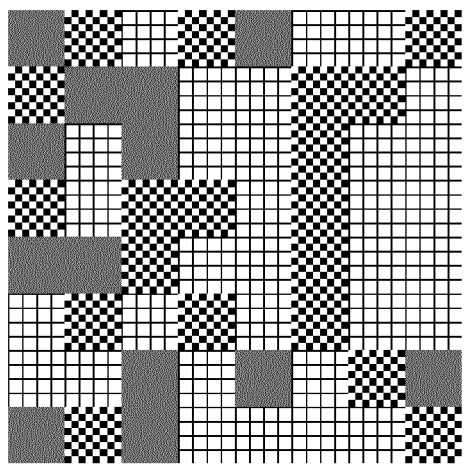
FIG. 4a: Synthetic image where the consisting squares are filled with three different patterns, simulating stained (color) tissue.
Figure 4B:
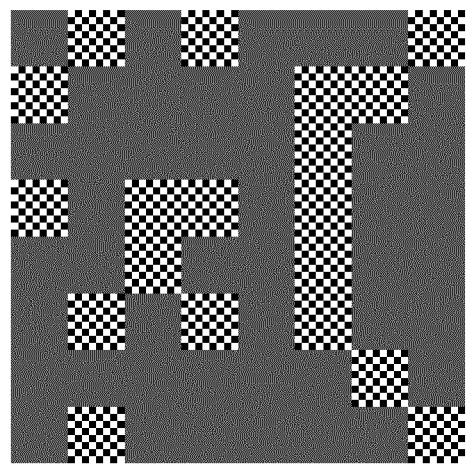
FIG. 4b-4d: Different color channels generated by processing the synthetic image of FIG. 4a according to a method of the present invention.
Figure 4C:
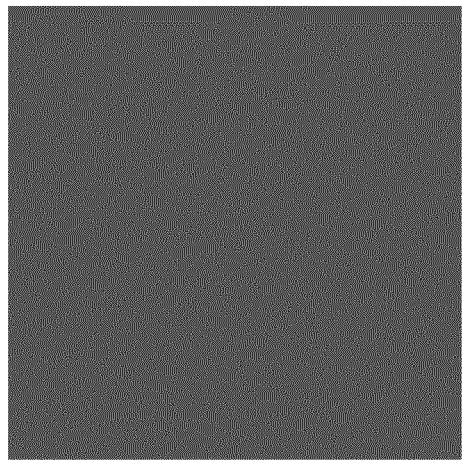
Figure 4D:
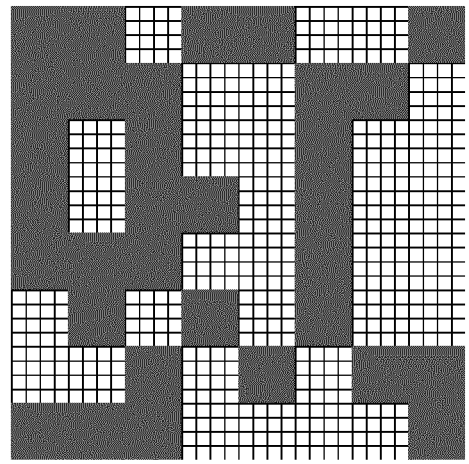
Figure 5A:
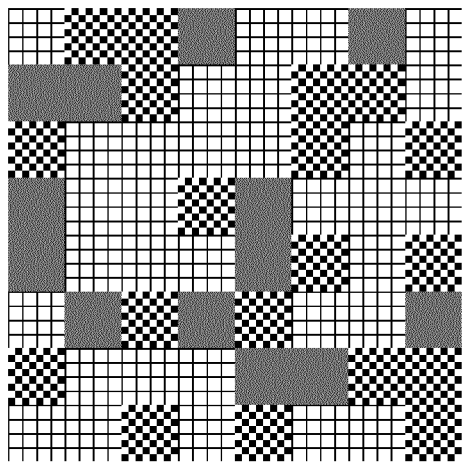
FIG. 5a: Synthetic image where the consisting squares are filled with three different patterns, simulating stained (color) tissue.
Figure 5B:
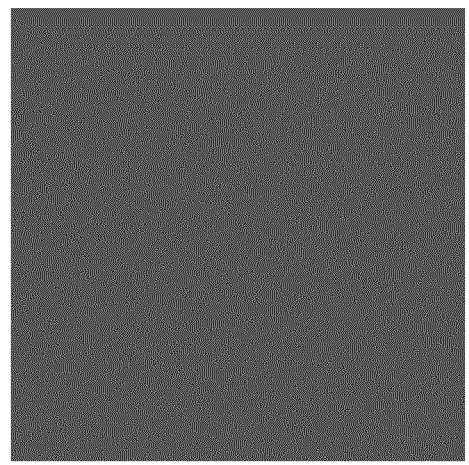
FIG. 5b-5d: Different color channels generated by processing the synthetic image of FIG. 5a according to a method of the present invention.
Figure 5C:
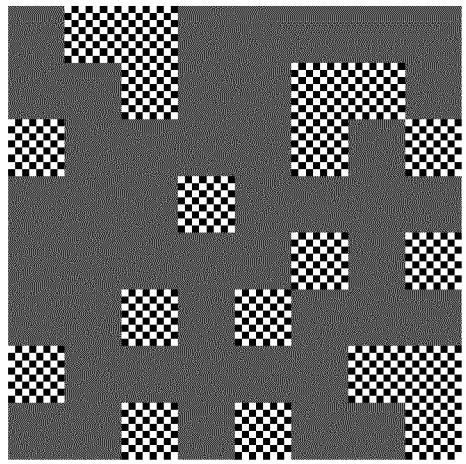
Figure 5D:
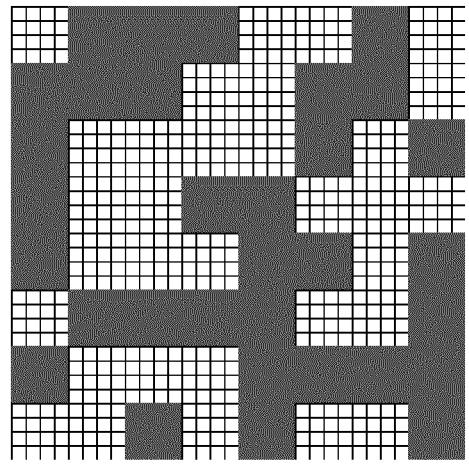

FIG. 4a shows a synthetic image (simulating stained tissue) where individual squares are filled with a checkerboard pattern, a square pattern, and a uniform gray pattern: the checkerboard pattern corresponds to the stain DAB (brown color), the square pattern to the counterstain hematoxylin (blue color), and the uniform gray pattern to the background. This synthetic image was processed with the method according to example B1a. For the decomposition step, $\mu_7$ is used for both f and g. The $q_+$ image is computed with FIG. 4b-d showing the red, green, blue channel, respectively. The red channel comprises pixels that are brown (checkerboard pattern) in the original image, and the blue channel comprises pixels that are blue (square pattern) in the original image. Thus, in the red and blue channels the colors (of stain DAB and counterstain hematoxylin) are exactly separated. This is even the case when the stain and counterstain are not exactly brown or blue, but each have a color within a certain intensity range of brown and blue (representing the experimental variations that can occur during the staining process).

FIGS. 5a-d show a similar example, where a synthetic image (simulating stained tissue) was processed by the method according to example B1a. The synthetic image comprises pixels in green (checkerboard pattern) for the stain Vina Green, blue for the counterstain hematoxylin (square pattern), and the uniform gray pattern for background. The same decomposition with $\mu_7$ for f and g was applied. The green channel comprises pixels that correspond to the stain Vina Green (checkerboard pattern) in the original image, and the blue channel comprises pixels that correspond to the counterstain hematoxylin (square pattern).

The method according to example B1a with $\mu_7$ for f and g can be used for separating colors of other stains as well, such as Fast Red/hematoxylin or hematoxylin and eosin (H&E) stains, etc.

Figure 6A:
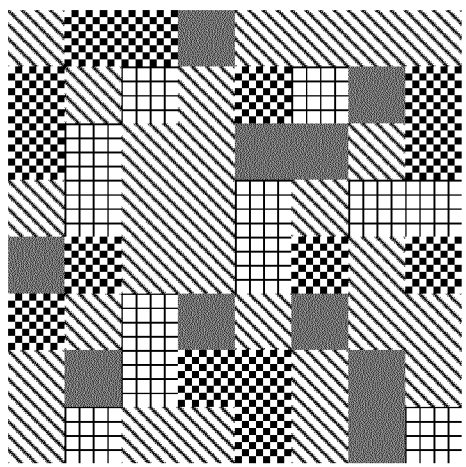
FIG. 6a: Synthetic image where the consisting squares are filled with four different patterns, simulating stained (color) tissue.
Figure 6B:
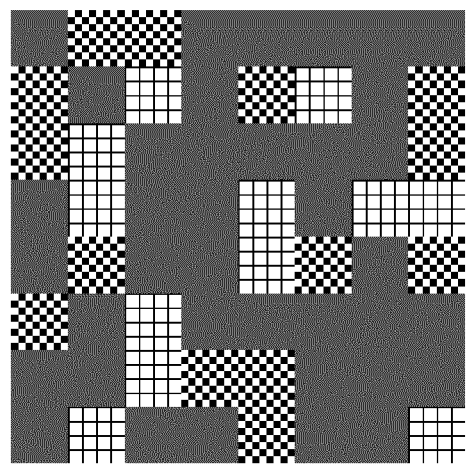
FIG. 6b-6d: Different color channels generated by processing the synthetic image of FIG. 6a according to a method of the present invention.
Figure 6C:
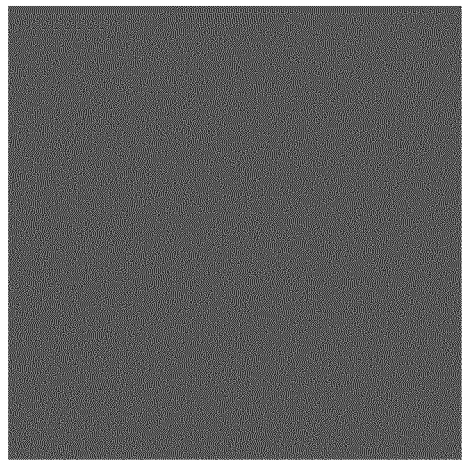
Figure 6D:
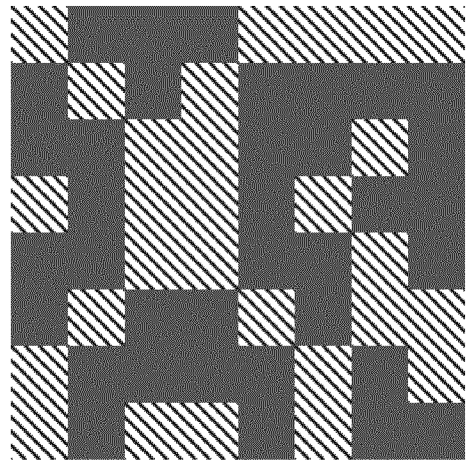

The method can be used for visualizing a double stain. FIG. 6a shows a synthetic image (simulating stained tissue) where the squares are filled with the color brown for the stain DAB (checkerboard pattern), a light red for the stain Fast Red (square pattern), blue for the counterstain hematoxylin (diagonal pattern), and the uniform gray pattern for background. Also, this image was processed by the method according to example B1a. FIG. 6b shows the red channel comprising pixels of the stain DAB (checkerboard pattern) and the stain Fast Red (square pattern). The blue channel comprises pixels corresponding to the counterstain hematoxylin (diagonal pattern).

The method was successfully applied to real-world images with the aforementioned stains. In color channels R, G, and B different stains were successfully separated.

A third example B1b is a further method for separating certain colors in an image:

Input a color image (elements $\in \mathbb{R}$) and convert to a quaternion matrix and then perform the following operation element-wise (q elements $\in \mathbb{H}$): [ln(q) exp (q)].

Convert to an n×m×3 array and normalize its values to the range 0 to 1 using the minimum and maximum values of each consisting matrix (n, m elements $\in \mathbb{R}$).

Convert to a quaternion matrix (elements $\in \mathbb{H}$).

Perform the orthogonal planes split using any pure unit quaternion combination of interest from $\mu_1$ to $\mu_{13}$ (elements $\in \mathbb{H}$).

Convert the quaternion matrix to three real matrices corresponding to the three-color channels R, G, and B (elements $\in \mathbb{R}$).

Truncate the values of each matrix that are less than 0 to zero and those larger than 1 to one (elements $\in \mathbb{R}$).

Concatenate the three matrices into one and output a color image; color channels of output correspond to contribution of each stain (elements $\in \mathbb{R}$).

The method according to the third example B1b corresponds substantially to the method of second example B1a but differs only in the additional steps of converting to a quaternion matrix, performing an element-wise operation, and then converting to an n×m×3 array and normalizing its values. These additional steps have the effect that an inhomogeneous gray background is converted to a homogeneous black background. This makes the separation step more efficient.

A fourth example B1c is a further method for separating certain colors in an image:

Input a color image (elements $\in \mathbb{R}$) and convert to a quaternion matrix (elements $\in \mathbb{H}$).

Perform the orthogonal 2D planes split using values interactively determined by the user (e.g. point or area sampling) or computed by an automated method (elements $\in \mathbb{H}$): $q_+ = \frac{1}{2}(q + s_1 q s_2)$ with $s_1$, $s_2$: vectors of stain 1 and stain 2.

Convert quaternion matrix to three real matrices corresponding to the three-color channels R, G, and B (elements $\in \mathbb{R}$).

Truncate the values of each matrix that are less than 0 to zero and those larger than 1 to one (elements $\in \mathbb{R}$).

Concatenate the three matrices into one and output a color image; color channels of output correspond to contribution of each stain (elements $\in \mathbb{R}$).

The fourth example B1c corresponds substantially to the method of second example B1a but differs only in the way of performing the orthogonal 2D planes split. For the split, the vectors $s_1$, $s_2$ are used instead of the pure unit quaternions $\mu_1$ to $\mu_{13}$. The vectors $s_1$, $s_2$ describe two colors of the image: colors of stain 1 and stain 2. With this decomposition the colors in the image corresponding to $s_1$ and $s_2$ are emphasized.

The color vectors can be interactively determined by the user, e.g. by selecting pixels from the original image that correspond to the colors of the stains. Additionally, it is possible to use an automated method for computing the color vectors; this has the advantage that the colors can be obtained efficiently. In all aforementioned examples, the vectors $s_1$, $s_2$ can be utilized instead of the pure unit quaternions $\mu_1$ to $\mu_{13}$.

The above-mentioned examples can be modified in different ways. For instance, it is possible to exchange the truncation with the normalization step in the third and fourth example. It is also possible to execute a visualization method according to the first example A1 with an appropriate choice of pure unit quaternions, followed by a separation workflow according to the second to fourth example.

In a multistage approach, for double, triple, or multiplex stains several separation methods can be combined. One or more separation methods can follow a visualization method according to the first example A1 with an appropriate choice of pure unit quaternions or color vectors $s_1$, $s_2$ for each stain contribution and background stain. Such visualization method changes the colors of the original image which allow a more efficient separation. The separation can be carried out according to the second to fourth example (B1a to B1c).

For instance, for a double stain with brown-stained and red-stained cell structures and blue-stained cell nuclei as background, different methods can be combined to separate the stains: i) a visualization method according to the first example A1 is carried out so that only the brown and red stain appear in the image but with different colors, and then separation is done using any of the examples B1a to B1c; ii) a visualization method according to the first example A1 is performed so that only the red stain appears in the image (everything else is background), and then separation is done using any of the examples B1a to B1c (similarly for the brown stain).

LIST OF REFERENCES 1 camera
2 computational unit
3 display unit
4 input unit
5 lens system
6 probe

The invention claimed is:

1. A method for color visualization and separation of a first image comprising pixels defined by color pixel vector $a=[a_1, a_2, a_3]$ in a Cartesian color space, the method comprising:

representing the color pixel vector by a pure quaternion $q=a_1 i+a_2 j+a_3 k$ with i, j, k satisfying:

$$i^2=j^2=k^2=ijk=-1, ij=-ji=k, jk=-kj=i, ki=-ik=j$$

decomposing the first image into $q_+$ and $q_-$ using the orthogonal 2D planes split concept according to:

$$q_+ = \tfrac{1}{2}(q+fqg), q_- = \tfrac{1}{2}(q-fqg)$$

wherein f and g are pure unit quaternions, or f and g describe interactively determined or computed colors ($s_1$, $s_2$), converting $q_+$ into first sets of first real numbers, the first sets corresponding respectively to color channels R (red), G (green), and B (blue) and converting $q_-$ into second sets of second real numbers, the second sets corresponding respectively to the color channels R, G, and B, processing the first real numbers and the second real numbers by:

normalizing the first real numbers and the second real numbers to a predefined range, or truncating the first real numbers and the second real numbers to zero if less than zero and truncating to one if greater than one, and outputting a second image as defined by the processed first real numbers and the processed second real numbers.

2. The method according to claim 1, wherein the determined or computed colors are colors contained in the first image.

3. The method according to claim 1, wherein f and g correspond to one or more of the following pure unit quaternions:

$$\mu_1 = i, \mu_2 = j, \mu_3 = k, \mu_4 = \frac{i+j}{\sqrt{2}}, \mu_5 = \frac{i+k}{\sqrt{2}}, \mu_6 = \frac{j+k}{\sqrt{2}},$$

$$\mu_7 = \frac{i+j+k}{\sqrt{3}}, \mu_8 = \frac{-i+j}{\sqrt{2}}, \mu_9 = \frac{-i+k}{\sqrt{2}}, \mu_{10} = \frac{-j+k}{\sqrt{2}},$$

$$\mu_{11} = \frac{-i+j+k}{\sqrt{3}}, \mu_{12} = \frac{i-j+k}{\sqrt{3}}, \mu_{13} = \frac{i+j-k}{\sqrt{3}}.$$

4. The method according to claim 3, wherein f and g are pure unit quaternions $\mu_a$ or $\mu_a\mu_b$ or, $\mu_a\mu_b\mu_c$ where a, b, and c are integers from 1 to 13.

5. The method according to claim 1, wherein the color space is Cartesian.

6. The method according to claim 1, further comprising repeating the decomposing, converting, processing, and outputting steps for different values off and g.

7. The method according to claim 1, further comprising performing color visualization and separation in the fields of medical image analysis, scientific research, social media, multimedia and graphics, aeronautics, deep sea and space exploration, or computational photography.

8. A software module, wherein the software module is implemented to carry out the method according to claim 1 when executed on a computational unit.

9. A device for image analysis, comprising: a camera, a computational unit, a display unit and an input unit, wherein the computational unit comprises the software module according to claim 8.

10. An integrated circuit, wherein the integrated circuit is implemented to carry out the method according to claim 1.

11. A device for image analysis, comprising: a camera, a computational unit, a display unit and an input unit, wherein the computational unit (2) comprises the integrated circuit according to claim 10.

12. The method according to claim 1, further comprising displaying the second image via a display unit.

13. The method according to claim 1, further comprising concatenating the processed first real numbers and the processed second real numbers into a matrix.

14. The method according to claim 1, wherein processing the first real numbers and the second real numbers comprises normalizing the first real numbers and the second real numbers to a predefined range.

15. The method according to claim 14, wherein processing the first real numbers and the second real numbers further comprises truncating the first real numbers and the second real numbers to zero if less than 0 and truncating to one if greater than 1.

16. The method according to claim 1, wherein processing the first real numbers and the second real numbers comprises truncating the first real numbers and the second real numbers to zero if less than 0 and truncating to one if greater than 1.

17. The method according to claim 1, wherein the color space is RGB.

18. The method according to claim 1, wherein the determined or computed colors are colors contained in the first image, wherein $f=g$.

19. The method according to claim 1, wherein the determined or computed colors are colors contained in the first image, wherein $f \neq g$.

* * * * *